(12) United States Patent
Chen et al.

(10) Patent No.: US 7,126,681 B1
(45) Date of Patent: Oct. 24, 2006

(54) CLOSED REGION DEFECT DETECTION SYSTEM

(75) Inventors: George Q. Chen, Fremont, CA (US); Lih-Huah Yiin, Mountain View, CA (US); Yu Cao, Cupertino, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 320 days.

(21) Appl. No.: 10/421,626

(22) Filed: Apr. 23, 2003

Related U.S. Application Data

(60) Provisional application No. 60/375,091, filed on Apr. 23, 2002.

(51) Int. Cl.
*G01N 21/00* (2006.01)

(52) U.S. Cl. .................................. 356/237.4; 356/237.5

(58) Field of Classification Search .. 356/237.1–237.5, 356/239.1–239.8
See application file for complete search history.

(56) References Cited

U.S. PATENT DOCUMENTS

| | | | | |
|---|---|---|---|---|
| 4,247,203 A | * | 1/1981 | Levy et al. | 356/398 |
| 5,131,755 A | * | 7/1992 | Chadwick et al. | 356/446 |
| 5,966,677 A | * | 10/1999 | Fiekowsky | 356/241.1 |
| 6,141,038 A | * | 10/2000 | Young et al. | 348/126 |
| 6,411,377 B1 | * | 6/2002 | Noguchi et al. | 356/237.4 |
| 6,539,331 B1 | * | 3/2003 | Fiekowsky | 250/548 |
| 6,727,987 B1 | * | 4/2004 | Yonezawa | 356/237.2 |
| 6,829,047 B1 | * | 12/2004 | Fujii et al. | 356/237.4 |

* cited by examiner

*Primary Examiner*—Layla G. Lauchman
*Assistant Examiner*—Gordon J. Stock, Jr.
(74) *Attorney, Agent, or Firm*—Smyrski Law Group, AP.C

(57) ABSTRACT

A method and apparatus for inspecting specimens or patterned transmissive substrates, such as photomasks, for unwanted particles and features, particularly those associated with contacts, including irregularly shaped contacts. A specimen is illuminated by a laser through an optical system comprised of a laser scanning system, individual transmitted and/or reflected light collection optics and detectors collect and generate signals representative of the light transmitted by the substrate. The defect identification of the substrate is performed using those transmitted light signals. Defect identification is performed using an inspection algorithm by comparing image feature representations of a test specimen with a reference specimen, and using a boundary computer and flux comparison device to establish tight boundaries around contacts and compute flux differences between the test and reference specimen contacts. Defect sizes are reported as ratio of flux difference, and entire contacts are highlighted for review.

14 Claims, 10 Drawing Sheets

CLOSED REGION DEFECT DETECTION SYSTEM

This application claims the benefit of U.S. Provisional Patent Application Ser. No. 60/375,091, filed Apr. 23, 2002.

BACKGROUND OF THE INVENTION

1. Field of the Invention

The present invention relates generally to electro-optical inspection systems, and more particularly to a method or algorithm for automated photomask inspection to detect defects on optical masks, reticles, and the like.

2. Description of the Related Art

Integrated circuits are made by photolithographic processes which use photomasks or reticles and an associated light source to project a circuit image onto a silicon wafer. A high production yield is contingent on having defect free masks, reticles, and wafer surfaces.

Automated mask inspection systems have existed for several years. One of the earliest such systems used a laser that scanned the mask. Subsequent systems used a linear sensor to inspect an image projected by the mask using die-to-die inspection, i.e., inspection of two adjacent dice by comparing them to each other. Other systems have been developed that teach die-to-database inspection, i.e. inspection of the reticle by comparison to the database from which the reticle was made.

As the complexity of integrated circuits has increased, so has the demand on the inspection process. Both the need for resolving smaller defects and for inspecting larger areas have resulted in much greater speed requirements, in terms of number of pixel elements per second processed. The increased demands have given rise to improvements described in various publications and issued patents.

Photomasks are used in the semiconductor manufacturing industry for the purpose of transferring photolithographic patterns onto a substrate such as silicon, gallium arsenide, or the like during the manufacture of integrated circuits. The photomask is typically composed of a polished transparent substrate, such as a fused quartz plate, on which a thin patterned light blocking layer, consisting of figures, has been deposited on one surface. The patterned light blocking layer is typically chromium with a thickness of 800 to 1300 angstroms. This layer may have a light anti-reflection coating deposited on one or both surfaces of a patterned material, such as chromium, MoSi, or other material. In order to produce functioning integrated circuits at a high yield rate, the photomasks and the resultant semiconductor wafer surfaces must be free of defects. A defect is defined here as any unintended modification to the intended photolithographic pattern caused during the manufacture of the photomask or as a result of the use of the photomask. Defects can be due to a variety of circumstances, including but not limited to, a portion of the light blocking layer being absent from an area of the photolithographic pattern where it is intended to be present, a portion of the light blocking layer being present in an area of the photolithographic pattern where it is not intended to be, chemical stains or residues from the photomask manufacturing processes which cause an unintended localized modification of the light transmission property of the photomask, particulate contaminates such as dust, resist flakes, skin flakes, erosion of the photolithographic pattern due to electrostatic discharge, artifacts in the photomask substrate such as pits, scratches, and striations, and localized light transmission errors in the substrate or light blocking layer.

During the manufacture of photomasks, automated inspection of the photomask is performed in order to ensure freedom from the aforementioned defects. There are various methods for the inspection of patterned masks, reticles, or the wafer surface currently available. One of those inspection methods is a die-to-die comparison which uses transmitted light to compare two adjacent dies. These comparison-type inspection systems are quite expensive because they rely on pixel-by-pixel comparison of all the dies and, by necessity, rely on highly accurate methods of alignment between the two dies used at any one time for the comparison. Apart from their high costs, this method of inspection is also unable to detect particles on light blocking parts of the reticle which have the tendency to subsequently migrate to parts that are transparent and then cause a defect on the wafer.

Another method for inspecting patterned masks or wafers is restricted to locating particulate matter on the mask or wafer. It makes use of the fact that light scatters when it strikes a particle. Unfortunately, the edges of the pattern also cause scattering and for that reason these systems can in certain circumstances be unreliable for the detection of particles smaller than one micrometer.

Even with these newer photomask and wafer inspection techniques, it has discovered that certain aspects of the patterned wafer may present specific inspection challenges. For example, different wafer layers may include certain contacts, which are openings or holes in the layer enabling connection between transmissive elements on layers adjacent to the contact. In the case of contacts, small imprecisions in creation thereof may significantly harm the transmissive properties of the contact and should be avoided. The nature of contact creation is such that even small errors create large problems with transmissivity, and thus small errors in contact formation tend to have significantly larger adverse consequences than, for example, the presence of particles on the surface. A further problem with contact formation and errors associated with contacts is that or identifying contacts in the first place, as well as comparing a contact to known contacts. With respect to contact comparison, previous attempts to identify errors in contact formation used what was known as a "golden contact," or ideal contact for comparison. The golden contact would have ideal properties and an inspected contact would be compared to the golden contact in a pixel-by-pixel comparison. In practice, however, the shape of the contact might be such that it had acceptable transmissive properties, but was somehow misshapen as a result of the fabrication process. Such a misinterpretation of the electrical properties of the contact would result in a good contact being classified as bad. Alternately, the pixel-by-pixel comparison depends on certain tolerance settings, and bad contacts could be flagged as good if the contacts fall within acceptable tolerance levels but ultimately fail to provide adequate transmissiveness characteristics. Further, contacts may intentionally have sizes and shapes which differ significantly from an ideal contact.

It would be beneficial to provide a system which did not include the drawbacks associated with previous contact inspection systems.

SUMMARY OF THE INVENTION

The present system has the ability to simultaneously detect defects, particularly those associated with contacts on the surface of test and reference specimens, such as photomasks, using transmitted and/or reflected light energy or flux received. In accordance with the present invention there is provided a novel method and apparatus for the inspection of photomasks at a high sensitivity to detect submicron particulate contamination, chemical stains and residues, pattern errors such as CD error, localized transmission variations, and so forth, by utilizing synchronized transmitted and/or reflected light signals (i.e. from the same location on the substrate with either the same light beam or two light beams of equal intensity and cross sectional size and shape illuminating the same location on the substrate).

The present system may be employed in conjunction with an inspection system that employs inspection techniques using transmitted and reflected light. Such a system may create a two dimensional mapping of transmitted and reflected light scans of the specimen, where the transmitted scan and the reflected scan are performed simultaneously, near simultaneously, or staggered in time from one another. The design presented herein may be employed in such a system without using two-dimensional mapping, or it may be used in addition to the two dimensional mapping or to enhance the results of the two dimensional mapping using transmitted and reflected scans. Further, the present system may use reflected light signals to determine the validity of a contact rather than or in addition to transmitted energy signals.

Further there is provided a closed region defect detection algorithm for a plurality of images scanned, such as a test and reference image, to determine defects at and around certain features on the specimen, such as contacts. The system samples transmitted images for a reference and test specimen and establishes a set of contact zones on the specimens. The system then establishes a tight set of boundaries on those regions determined to be contacts, based on transition characteristics of the scanned images. These boundaries are identical on both the reference and test specimen. The system then computes the flux differences between the bounded regions in a pixel by pixel comparison of the intensities in the zones, and may determine a percentage difference or difference range to identify the likelihood of a defect in the contact region for the test and reference specimen. Thresholding may be employed to identify defects and establish boundaries in the system disclosed. The invention can further include simultaneously inspecting for contamination using the transmitted and reflected light and variations thereon as shown, for example, in U.S. Pat. No. 5,563,702, inventor David G. Emery, issued Oct. 8, 1996, or U.S. Pat. No. 6,282,309, inventor David G. Emery, issued Aug. 28, 2001, while also processing the transmitted light for contact flux/energy measurements.

According to a first aspect of the present invention, a method for inspecting a plurality of specimens is provided, with each specimen having at least one feature located thereon. The method comprises scanning each specimen, thereby establishing a plurality of points, each point having an intensity associated therewith, determining bounded regions wherein said intensities differ relatively significantly from other regions, calculating a flux based on intensities associated with all specimens, and determining defective features on the specimens based on the flux difference between the specimens.

According to a second aspect of the present invention, a method for determining contact defects in a plurality of semiconductor wafer masks is provided. The method comprises scanning the semiconductor wafer masks using transmitted light energy, resulting in scanned representations of the semiconductor masks, aligning the scanned semiconductor masks, selecting approximate potential problem areas on said plurality of scanned semiconductor masks, establishing a set of narrower boundaries for said potential problem areas within each of said scanned semiconductor masks, wherein the establishing comprises locating demarcations of intensity variations, and comparing fluxes between said sets of narrower boundaries to determine contact defects.

According to a third aspect of the present invention, a system for determining defects in a plurality of specimens is provided, the system comprising a light emitting device transmitting light energy toward each specimen, at least one sensor for sensing transmitted light energy received from each specimen. The sensor transmits a light intensity representation of one specimen to a computing device. The computing device comprises an aligner for aligning the light intensity representations of a plurality of specimens, a critical point selector for selecting general areas for detailed inspection on said light intensity representations of a plurality of specimens, a boundary device for creating a set of narrow boundaries around each of said critical points based on light intensity transitions, and a flux computer for computing the flux associated with the critical points within the narrow boundaries of the light intensity representations.

These and other objects and advantages of all of the aspects of the present invention will become apparent to those skilled in the art after having read the following detailed disclosure of the preferred embodiments illustrated in the following drawings.

DETAILED DESCRIPTION OF THE INVENTION

Figure 10:
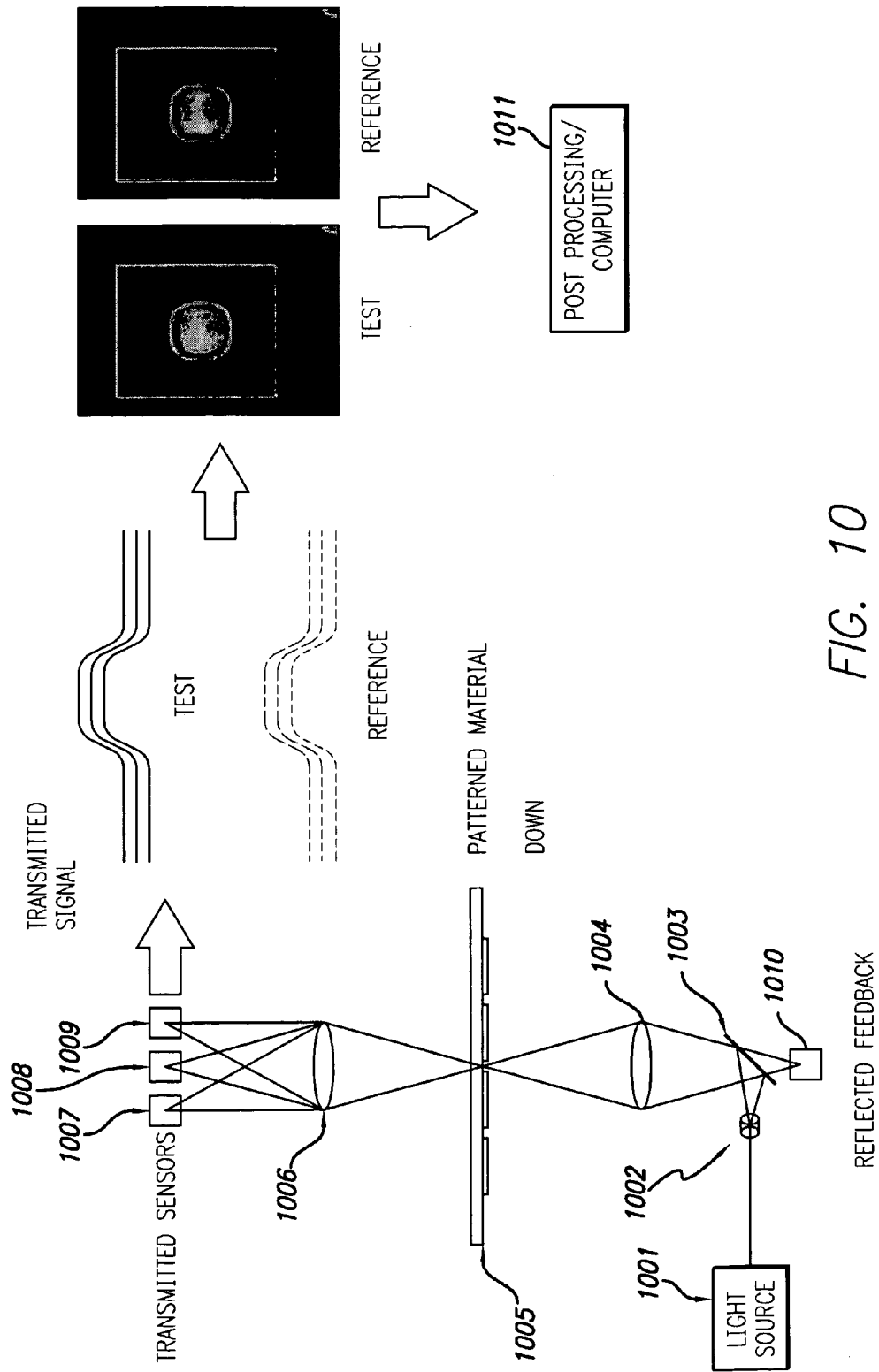
FIG. 10 is a general representation of a system employing the current design.

A general representation of a system employing the current design is presented in FIG. 10. From FIG. 10, a light source 1001 emits light energy or flux toward a set of lenses 1002, which expands the light energy toward a beamsplitter/reflector 1003. The light may be any form of radiation, including but not limited to laser light, sufficient to illuminate the wafer and be detected by the sensors 1007–1009. Light energy is reflected to lens or lensing arrangement 1004, and to the specimen, such as a wafer 1005, where in the case of a wafer the patterned side is downward in the orientation shown. The patterned side is in certain circumstances referred to as the chrome side or metal side, but other materials may be used. The opposite side of the wafer or specimen typically is composed of a transparent or semitransparent material, commonly referred to as glass. In this configuration, light exposure of the specimen will reflect from the patterned material and pass through areas where no patterned material is present after passing through the glass or transparent/semitransparent material. From the wafer 1005 or specimen, light may pass to a second lens or lensing arrangement 1006 and be transmitted to transmitted sensors 1007–1009. These sensors may be any appropriate type of sensor, including but not limited to TDI sensors and CCD sensors. More or fewer than three sensors may be employed. The photomask, wafer, or specimen 1005 may be passed linearly perpendicular to the line of light. In the instance where light strikes the patterned material on the photomask 1005, that beam is reflected back through lens 1004 and passes through beamsplitter/reflector 1003, directing some light toward reflected feedback element 1010. Some light is reflected back toward the light source 1001 in this orientation. Reflected feedback element may be any appropriate element, including a sensor or a light capturing device.

The present design may employ two dice, one a reference die and one a test die on one photomask, that generates two patterns on the wafer or specimen surface. More dice may be employed. The result of using two or more dice is a test and a reference signal being generated when scanned by the system presented in FIG. 10. The two signals may have particular characteristics, and in the case of a contact, the test and reference images sensed by sensors 1007 through 1009 may appear as shown in FIG. 10. It should be noted that the sensors 1007–1009 receive light and transmit signals representing light intensity, represented by the Test and Reference transmitted signals shown in FIG. 10. These signals are the result of either two separate scans, one of the Test photomask pattern on the specimen and one of the Reference photomask pattern on the specimen. Alternately, multiple scanning devices similar or identical to that represented in FIG. 10 may be employed, which may increase system cost but may provide exposure to more uniform light illumination than two separate scans of the two separate surfaces.

In the present design, reflected light may be collected by, for example, element 1010, and employed in the flux determination aspect of the invention described below. Collection and use of reflected energy may be as an alternative or in addition to the collection and use of transmitted energy in determining the flux characteristics of the specimen.

The representation of FIG. 10 is a generalized representation of a system which may employ the current invention. The functionality critical to the present invention is that of providing light intensity to the transmitted sensors such that the contacts or other holes or indentations may be differentiated from the pattern imparted on the wafer or specimen.

Other mechanizations besides that presented in FIG. 10 may be employed with similarly beneficial results. One specific system that may employ the current design is presented below. A block diagram of an automatic optical inspection system is shown at 10. The system is capable of inspecting substrates, such as reticles, photomasks, and semiconductor wafers.

Other arrangements that may be employed in association with the current invention include but are not limited to the designs disclosed in U.S. patent application Ser. No. 09/636,124, filed Aug. 10, 2000, and U.S. patent application Ser. No. 09/636,129, filed Aug. 10, 2000, both of which are assigned to the assignee of the present application. Both of the aforementioned applications are hereby incorporated by reference. Alternately, the system as disclosed herein may be operated in conjunction with devices employing near simultaneous transmitted and reflected inspection techniques, such as that disclosed in U.S. Pat. No. 5,892,579, entitled "Optical Inspection Method and Apparatus," issued Apr. 6, 1999.

The invention can further include simultaneously inspecting for contamination using the transmitted and reflected light and variations thereon as shown, for example, in U.S. Pat. No. 5,563,702, inventor David G. Emery, issued Oct. 8, 1996, and/or U.S. Pat. No. 6,282,309, inventor David G. Emery, issued Aug. 28, 2001, while also processing the transmitted light for contact flux/energy measurements as described herein.

Figure 1:
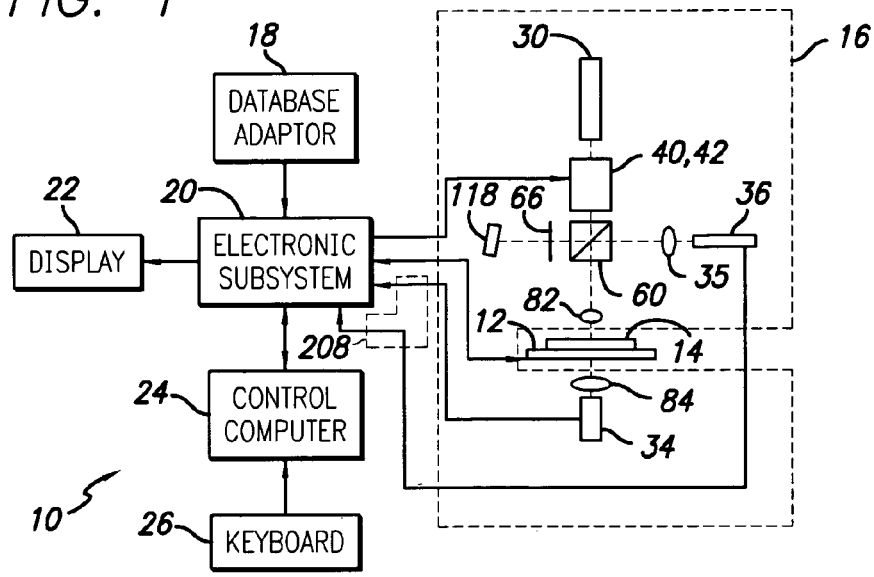
FIG. 1 is a simplified functional block diagram of a representative inspection system in accordance with one possible implementation of the present invention.

The system can perform several types of inspection: transmitted light inspection, reflected light inspection, simultaneous reflected and transmitted inspection, and phase shift measurement. In transmitted light inspection, light impinges on the substrate, a photomask for example, and the amount of light transmitted through the mask is detected. In reflected light inspection, the light reflecting from a surface of the substrate under test is measured. As depicted in the simplified block diagram of FIG. 1, a preferred embodiment of the system 10 includes a stage 12 for carrying a substrate 14 to be inspected, an optical subsystem 16, a data base adaptor 18, an electronics subsystem 20, a display 22, a control computer 24 and a keyboard 26.

The Stage

Although a preferred embodiment of the stage 12 will be described in detail below, it suffices to say that the stage is a precision device driver under control of subsystem 20 and is capable of moving the substrate 12 under test in a serpentine fashion, within a single plane, relative to the optical axes of the optical subsystem 16 so that all or any selected part of the substrate surface may be inspected.

Optical Subsystem

Figure 2:
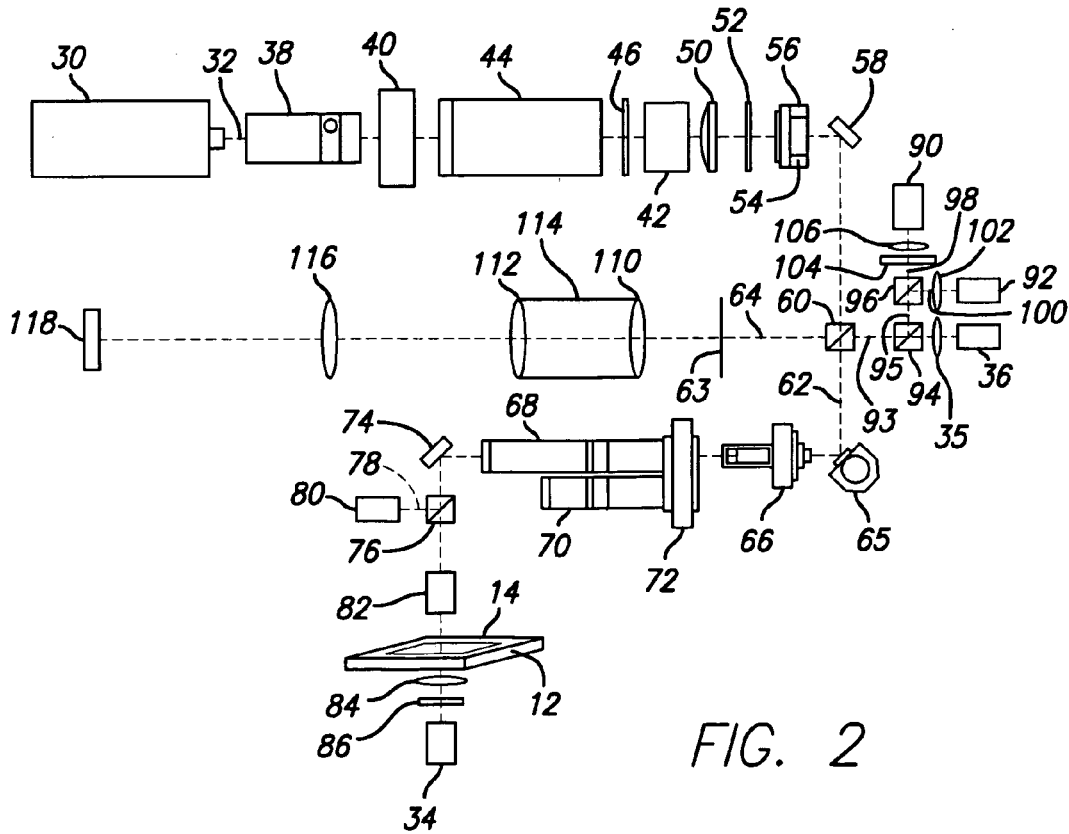
FIG. 2 is a more detailed schematic representation of the optical subsystem depicted in FIG. 1.
Figure 3:
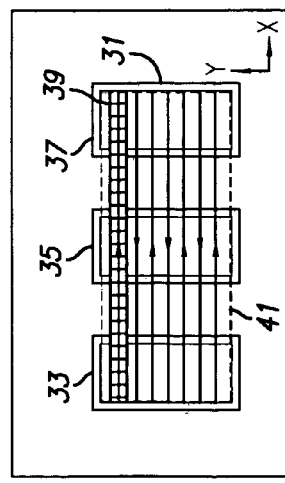
FIG. 3 is a diagram illustrating the scanning path used in the die-to-die inspection mode.
Figure 4:
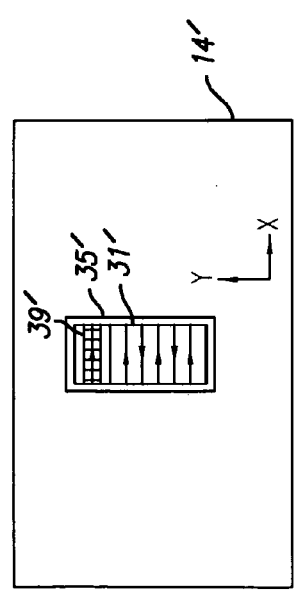
FIG. 4 is a diagram illustrating the scanning path used in die-to-database inspection mode.

A detailed block diagram of a representative optical subsystem 16 is shown in FIG. 2 and is essentially a laser scanner apparatus including a light source 302 and associated optics which cause a beam 32 of light to be deflected over a small angle, i.e., from one side to the opposite side of the optical axis defined by the optical subsystem 16. As will be further described below, the beam sweep is in a direction such that, after passing through the optical system, it is directed parallel to the Y-axis as viewed at the substrate 14. As the beam is swept, the stage 12 carrying the substrate 14 under test is caused to move back and forth in the direction of the X-axis, being incremented in the Y-direction at the end of each traverse so that the beam 32 is caused to sweep along a serpentine path 31 across a plurality of identified substrate subareas 33, 35, 37 (individual dice in the case of a photomask) as indicated in FIGS. 3 and 4. In this manner the entire surface area of the substrate (mask) 14 is swept in a series of contiguous swaths 39 by the light source or laser beam. In the case of a transparent or partially transparent substrate, detection of the image is accomplished by a transmission detector 34. In the case of a reflective or partially reflective substrate, the light reflected from the substrate is detected by a reflected light detector 36.

The light source 30 of the system may be a laser, or other appropriate light emitting device, such as the Model 5490A5L-00C-115 made by Ion Laser Technology of Salt Lake City, Utah. The light beam 32, emitted by the laser 30, first passes through a spatial filter 38 and is then deflected by the combination of two acousto optic elements; an acousto-optic prescanner 40 and an acousto-optic scanner 42. These two elements deflect the light beam in the Y-direction and focus it in the X-direction in a manner similar to that described in U.S. Pat. No. 3,851,951. (Jason H. Eveleth, "High Resolution Laser Beam Recorder with Self-focusing Acousto-optic Scanner", issued Dec. 3, 1974). The deflection system also may include a beam expander 44 and a quarter wave plate 46.

When the beam emerges from the scanner 42, it is convergent in the Y-direction, but collimated in the X-direction. A cylindrical lens 50 may then also focus the beam in the X-direction, with the focal plane for both X and Y axes lying at a field stop 52. The beam may next pass through a quarter wave plate 54 and a relay lens 56.

The beam may be reflected by a mirror 58, the sole function of which is to fold the optical path. The redirected beam may then enter a cube beam splitter 60 which divides it into paths 62 and 64. The latter path is used only in the phase measurement mode and is otherwise blocked by a shutter 63.

The beam continuing along path 62 is reflected by an oscillating mirror 65 which is held fixed during the inspection operation and is used only for displaying an image to an operator on an image display (not shown in FIG. 2) during alignment and review. A dove prism 66 may be used to rotate the direction of the scan about the optical axis. The output of prism 66 is fed to one of the telescopes 68 and 70 mounted on a rotatable turret 72. The purpose of these telescopes is to vary the size of the scanning spot on the substrate 14 and thereby allow selection of the minimum detectable defect size. Since changing the magnification also varies the length of the scan, the swath width is also changed and therefore the inspection speed. (Only two telescopes are shown but any number of telescopes, and therefore spot sizes, can be used.)

From the telescope the beam passes to a mirror 74 and then to a beam splitter 76 where the path is again split. The reflected portion of beam 78 is directed to a detector 80 which serves as a monitor of the beam intensity variation. The unreflected portion of the beam may pass through an objective lens 82 which focuses the beam onto the substrate 14. Light passing through the substrate 14 is then collected by a condenser lens 84 and a collector lens 86, and focused onto the transmission detector 34.

Transmission detector 34, instantaneously and continuously, generates a transmitted light signal 15 in proportion to the light transmitted through substrate 14 and received by transmission detector 34. Transmitted light signal 15 is then amplified and offset in electronic subsystem 20 to normalize the peak-to-peak signal amplitude to values of 0 to 1. Similarly reflected light detector 36, instantaneously and continuously, generates a reflected light signal 17 in proportion to the light reflected from substrate 14 and received by reflected light detector 36. Reflected light signal 17 is similarly normalized in electronic subsystem 20.

For purposes of discussion, substrate 14 is assumed to have a light blocking layer that covers a portion of the underlying material of substrate 14. That light blocking layer will reflect a greater portion of incident laser light 13 than is similarly reflected from the surface of the bare underlying material of the substrate. For example, it is known in the art that at a wavelength of 488 nm, anti-reflective chrome (light blocking layer) has a reflectance of 11% and quartz underlying material of a substrate has a reflectance of 4.5%.

Autofocus Subsystem

The autofocus function is based upon a monitoring of the shape of the light beam cross-section after it is passed through some anamorphic elements. The basic principle underlying the implementation is that a cylindrical lens produces astigmatism. In such a case a focussed beam first passes through best focus in one direction and then through best focus in the perpendicular direction. In between these two focal points along the beam path the beam cross section is oblong in one direction and transitions along the path through points where the beam cross section is circular and then oblong in a direction perpendicular to the previous direction. In this invention the optimum focus of the light impinging on the substrate is detected by monitoring the beam cross section of light reflected from the substrate 14. The shape of the beam cross section is monitored by two silicon quadrature photodiodes 90 and 92, such as made by Silicon Detector Corporation of Newbury Park, Calif.

As is explained in more detail below, the actual autofocus system may include two optical paths which differ from each other in the direction of the astigmation. In one path the cylindrical lens has no curvature when viewed in the X-direction while in the other path, the cylindrical lens has no curvature in the Y-direction.

Figure 5:
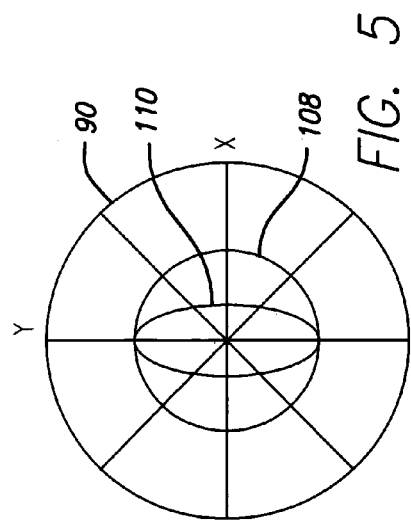
FIGS. 5 and 6 are diagrams illustrating possible beam cross sections used in the autofocus system.
Figure 6:
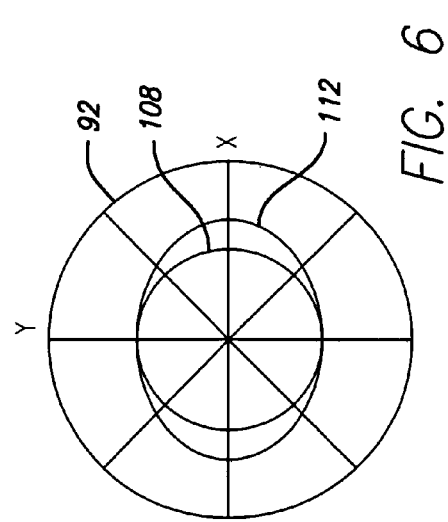

The autofocus beam 93 is split off from the reflected beam 95 directed along reflected detector path by a beam splitter 94, and is redirected toward another beam splitter 96 which splits the beam into two paths 98 and 100. In FIG. 2 the X-coordinate is perpendicular to the drawing and consequently, cylindrical lens 102 is shown with a curvature, while an identical element 104, in the other path, appears as a plano-parallel element. The path leading to detector 90 also contains a spherical lens, 106. The two identical quadrature detectors 90 and 92 detect a cross-section of each beam. As the substrate surface position, or thickness, varies, the beam cross section, as seen by the detectors, varies in the X-direction as shown in FIGS. 5 and 6 at 108, 110 and 108, 112 respectively. On neither detector does the vertical (Y-direction) diameter of the illuminated area change. When the mask is in focus, both detectors are illuminated by a circular beam 108. As the mask goes out of focus, the horizontal diameter shrinks on one detector (see FIG. 5), while on the other one it increases (see FIG. 6) as indicated by the outlines of the beam 110 and 112, respectively. This changes the electrical output from the quadrature detectors. The focus correction signal $F_c$ is then:

$$F_c = \frac{(A_1 - B_1) - (A_2 - B_2)}{(A_1 + B_1) + (A_2 + B_2)}$$

where $A_1$ is the signal derived from quadrants along the X axis of 90, $A_2$ is the signal derived from quadrants along the X axis of 92, $B_1$ is the signal derived from quadrants along the Y axis of 90, and $B_2$ is the signal derived from quadrants along the Y axis of 92.

Transmitted Light Inspection Mode

Ordinarily, transmission mode detection is used for defect detection on substrates such as conventional optical masks having transparent areas and light blocking areas. As the laser beam scans the mask, the light penetrates the mask at transparent points and is detected by transmitted light detector 34 which is located behind the mask 14 and measures the light collected by condenser lens 84 and collector lens 86.

Reflected Light Inspection Mode

Reflected light inspection is normally performed on light blocking substrates that contain image information in the form of developed photoresist features. Light reflected by the substrate passes backwards along the same optical path as described before but is then diverted by a polarizing beam splitter 60 into detector 36. A condenser lens 35 projects the light onto the detector 36. As previously stated, during reflected light inspection, shutter 63 is closed.

Reflected light inspection may also be used to detect contamination on top of light blocking substrate surfaces.

Simultaneous Detection by More than One Type of Detector

Transmitted and reflected light inspections and the contact measurement operation are not mutually exclusive in time. Simultaneous transmitted and reflected detection can disclose the existence of a light blocking defect sensed by the transmitted detector while the output of the reflected detector can be employed to disclose the type of defect. As an example, a chrome particle at an edge of a contact is light blocking and hence will result in a dark output from the transmission detector, but reflective chrome defects also produce a high reflected light indication while a particle will typically reflect less. By using both reflected and transmitted detection one may locate a particle on the edge of the patterned geometry. In general, one may determine signatures for certain types of defects, such as the ratio of their reflected and transmitted light intensities. This information can then be used to classify defects.

Similarly, transmitted light detection and contact measurement can occur simultaneously. A light blocking defect in a region covered by patterned material can be detected, and the absence of light blocking material detected by the transmitted light detector 34 can be used to determine the extent of the defect.

Control Computer

The control computer 24 acts as the operator console and master controller of the system and is a device such as a SPARC computer made by Sun Microsystems of Mountain View, Calif. All system interfaces with the operator and the user's facilities are made through the control computer. Commands are issued to and status is monitored from all other subsystems so as to facilitate completion of the operator assigned tasks.

Electronics Subsystem

The function of the electronics subsystem 20 is to interpret and execute the commands issued by control computer 24. These functions are: digitize the input from sensors, such as detectors 34 and 36; compensate these readings for variations in the incident light intensity; detect defects in the image and transfer the defect data to the control computer 24; accumulate the output of the interferometers used to track the stage 12; provide the drive for the stages linear motors; and monitor sensors which indicate status.

Except for the specific measurement, identification, quantification, and determination of contact information, the enumerated functions of control computer 24 and subsystem 20 have been generally described in, for example, U.S. Pat. Nos. 4,247,203, 4,579,455, 4,633,504, 4,805,123, 4,926,489, and 4,644,172. In the above patents the same functions are performed in many different ways and the particular approach adopted has depended on the availability and suitability of integrated circuit devices at the time the system was being developed. Any of the cited approaches or variations available to those of skill in the art could be used.

The Stage

The stage 18 may be an air-bearing X-Y stage that may be driven by a linear motor on each axis. The position of the stage along each axis is monitored by interferometers (not shown), such as the Model TIPS V, made by Teletrac Corporation.

Figure 7:
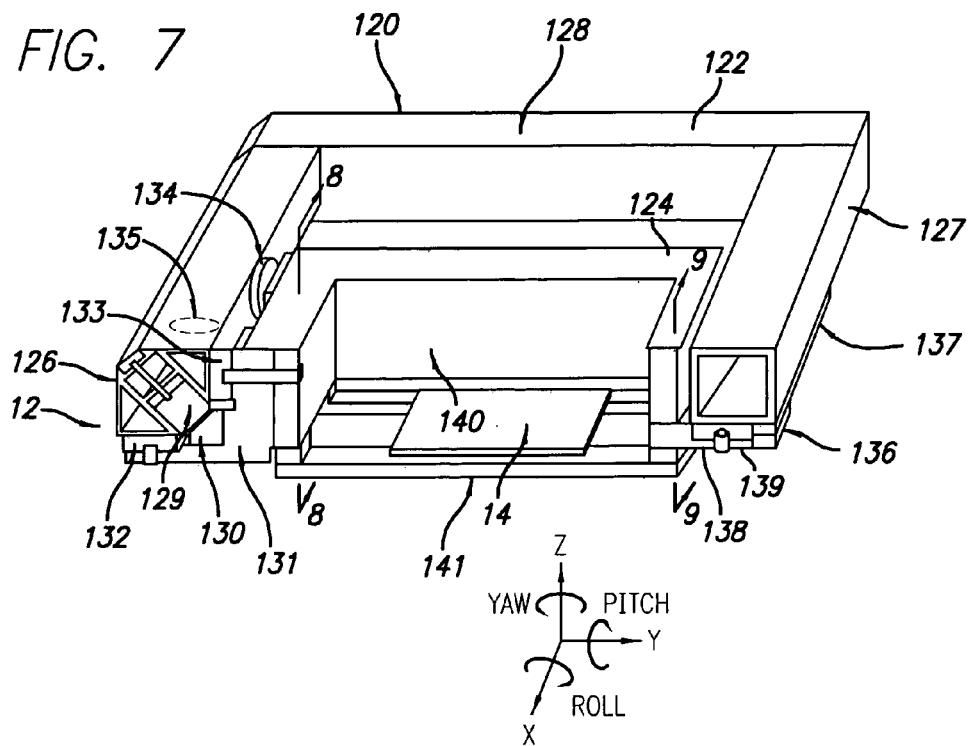
FIG. 7 is a partially broken perspective drawing illustrating the X-Y stage.

Stage 18 is shown in detail in FIG. 7 with the front rail cut away to permit view of the principle elements. The stage has two degrees of freedom; it has no rotational capability. It is disclosed here for application in the representative inspection system but could also be used in microlithography and any precision machining application.

The Y carriage 120, in the shape of a frame 122, carries the X stage 124. The motion of both stages is controlled by linear motors and air bearings. The attractive force between the stator and the slider of each linear motor provides the preload of the linear bearings.

The Y carriage frame includes two guideways 126 and 127, controlling the motion of the X stage 124 inside the carriage. The guideways are connected by two side rails 128. (The front rail, the equivalent of 128, is not shown.) The stator 129 of the X linear motor is imbedded inside the X guideway 126 in such a way that it attracts the X slider 130 attached to air-bearing housings 131 and preloads four of the five X air bearings 132, 133, 134 and 135. A separate magnet 136 and ferromagnetic preload strip 137 provide the preload to air bearing 138. Each bearing may be equipped with a swivel, enabling rotation of the bearing pad about two axes, in addition to rotating the bearing itself, thus the only degree of freedom constrained by an air bearing is the translation in the direction normal to the pad surface.

The X stage carries the specimen 14 and is kinematically constrained by the five air bearings: the bearings 132 and 135 control the pitch of the X stage motion, and constrain the vertical translation in the Z direction, bearings 133 and 134 control the yaw of the X motion and constrain the horizontal translation in the Y direction. Bearing 138 nested in the housing 139 controls the roll of the X stage and constrains vertical translation of the stage in the Z direction. The specimen holder assembly 140 may be attached to a lightweight composite frame 141 of the X stage.

Figure 8:
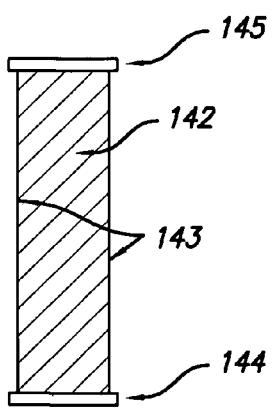
FIG. 8 is a cross-section taken along the line 8—8 of FIG. 7 showing details of the construction frame of the stage.

The stage contains a number of specific features. One such feature is the use of the linear motor to preload the stage in two directions and thereby achieve a relatively high level of stiffness. This is accomplished by the arrangement of triangular cross section slider iron 130 and angular position of the stator 131, so that the magnetic attraction force is at an angle to all four air bearings 132, 133, 134 and 135. Another feature of the design is that the stator 129 of linear motor is imbedded inside the guideway 126 at an angle to the two walls of the guideway. Also of note is the use of honeycomb material, such as Blue Seal, made by Hexcell of Dublin, Calif., for the construction of frame 140. This reduces the mass of the stage, yet makes it very rigid. A cross-section of this construction taken along the line 8—8 is shown in FIG. 8 where cellular insert 142 is sandwiched between skins 143. The bottom plate 144 and top plate 145 join the skins 143 and complete the box structure enclosing the insert 142. The honeycomb material may be replaced by any number of light composite materials, such as Duocell, manufactured by ERG of Oakland, Calif.

Figure 9:
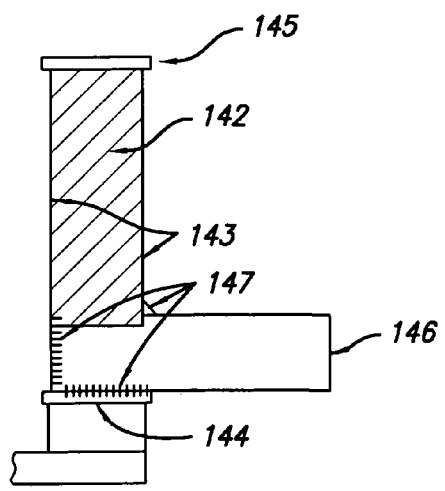
FIG. 9 is a cross-section taken along the line 9—9 of FIG. 7 showing other details of the construction frame of the stage.

Solid pieces 146 are attached to the composite such that they penetrate one skin of the composite wall and are attached to the opposite skin and either of the top or bottom plates, as shown in FIG. 9, with joints 147 formed around the penetration through the wall, and between the solid piece and the inside of the opposite skin and the plate 144.

Operation of the Representative System

Alignment

Prior to starting the automatic inspection operation, the operator aligns the mask in the proper orientation and defines to the computer the "care area," i.e., the area to be inspected. FIG. 3 illustrates the desired orientation of the inspection path 31 with respect to dice 33, 35, and 37 shown here on a multi-die mask or reticle 14. During inspection, the stage 12 is moved in a serpentine manner, following the path 31, while the laser beam is deflected parallel to the Y-axis of the mask. As stage 12 moves in the X-direction, this Y-axis motion of the laser beam sweeps out a swath, 39. Ordinarily the axes of mask 14 will not be parallel to the drive axis of the stage. Therefore, an X or a Y directional motion of the stage requires both of the drives of the stage to be driven simultaneously. The first task is therefore to define to the system the ratio of the speeds of the major axes of the stage. To accomplish this, the operator may choose two points known to him to lie on the same X-coordinate of the die. He may then drive the stage to these points, while observing the image on image display 22. The system may note the location of these points by measuring the travel with interferometers (not shown) along the drive axes of the stage. These measurements establish the direction cosines of the stage drive axes with respect to the X and Y axes of the mask. At this time the dove prism 66 (FIG. 2) is rotated to orient the deflection of the laser beam so that it is perpendicular to the X-directional travel of the stage. Next, the operator designates to the system the care area 41 (FIG. 3) of the die, the area to be inspected.

Measurement Calibration

Figure 11:
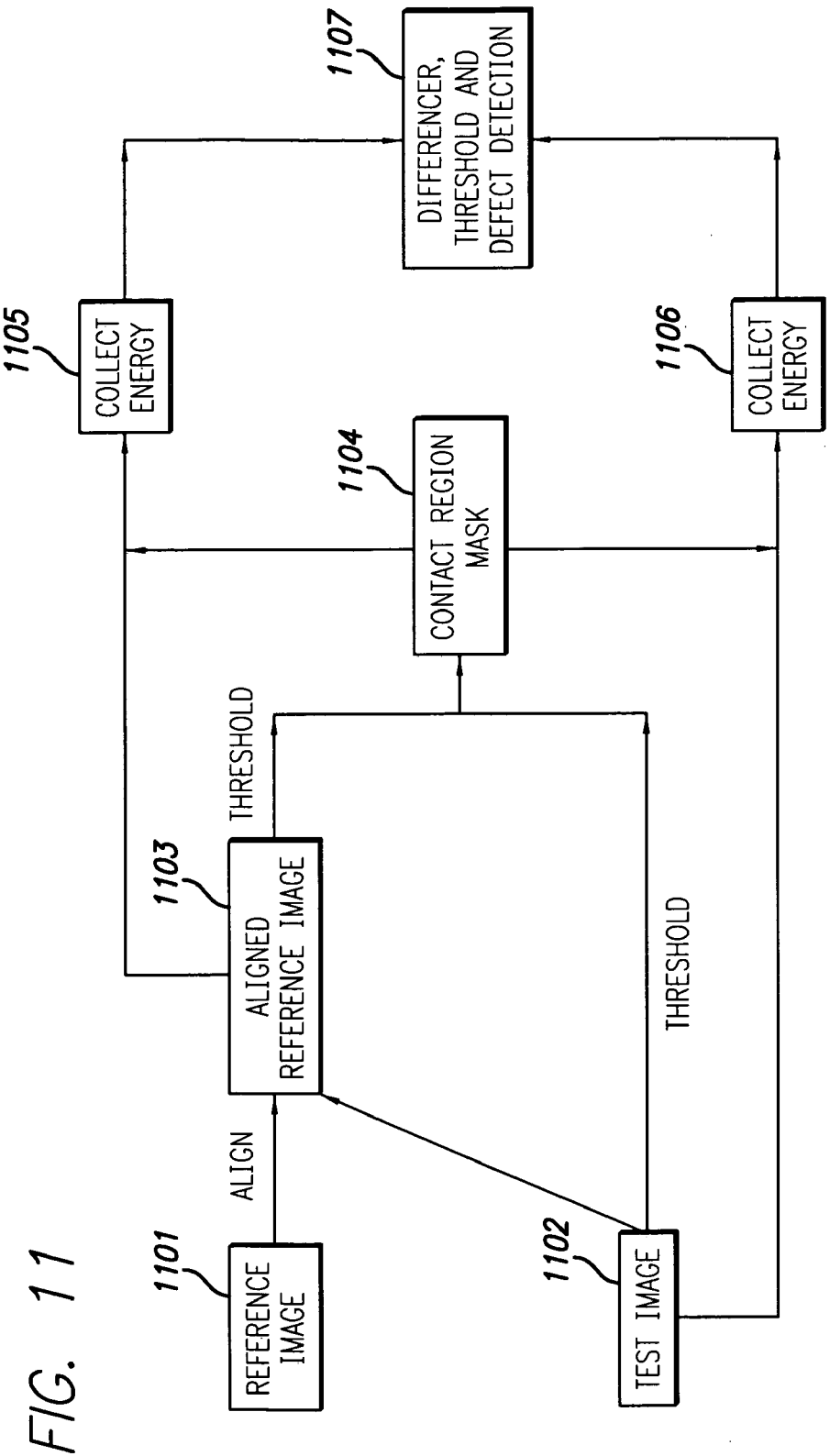
FIG. 11 is a flow diagram of the present system.

As the laser spot scans (in the Y-direction), a flat transparent surface parallel to the plane of the mask, the intensity varies sinusoidally, as shown by curve 200 in FIG. 11. Mathematically, the intensity I is:

$$I = A \sin[(2\pi y/w) - D)] + I_o$$

where y is the distance of the pixel in question from the origin, w is a constant that is a function of the tilt angle of mirror 118, D is the phase shift due to path length change as the result of the thickness of the phase shift material, A is the half-amplitude of the intensity, and $I_o$ is the intensity offset 204 due to stray light in the optics. These values are all determined during the phase shift measurement calibration part of the initialization. As the laser scans a flat uniform transparent area of the mask, the intensities at each picture element (pixel) are digitized and stored in the computer. Then, $I_o$ is the average value of the intensities over integer cycles, and A can be computed from:

$$A = (I_{max} - I_o)/2$$

The value W is the periodicity of the sinusoid.

$I_o$ and A are different for clear and phase shift material covered areas and therefore must be determined for both areas. The quantity D is a linear function of the thickness of the phase shift material and this relationship is determined by calibration on a known sample containing various thickness phase shift material features and remains constant while the system retains dimensional stability.

The Inspection Process

Automatic inspection of a reticle ordinarily starts at the upper left hand corner of the care area and follows the serpentine pattern 31 (see FIG. 3). As the stage slowly moves in the X direction, the light, such as a laser beam, rapidly sweeps in the Y-direction. In this manner a swath 39 is scanned and the digitized output of the detectors is stored in the electronics subsystem 20. When the swath reaches the left boundary of the care area of the second die 35, image data derived from die 33, and now stored in subsystem 20, is compared with the data derived from die 35. Subsequent processing is described below. In a similar manner, the data from die 37 may also be compared with the data derived from die 35.

When the scanning process reaches the right boundary of the care area of die 37, the stage is moved in the Y-direction an amount slightly less than the swath width and the stage starts a return trace in the X-direction. In this manner the care areas of the dice are traversed by the serpentine motion.

Die-to-database inspection, ordinarily performed on single die reticles, is similar to die-to-die inspection except that the comparison occurs between the die and a simulated image generated by database adaptor 18. FIG. 4 illustrates a die-to-database scan path 31'.

Review Operation

After completion of the automatic inspection operations, the operator may review the defects by causing control computer 24 to move the stage 12 to the area of a particular defect and hold it there. Alternately, post processing may be employed to identify, classify, and determine defects. If inspected by an operator, the image may be scanned by acousto-optic scanners 40 and 42 in the Y-direction and by oscillating mirror 65 in the X-direction, and the digitized image may be displayed on display 22. The operator may use the output of any of the detectors or the combination of outputs from more than one detector. If the operator desires, the different detector outputs may be superimposed and represented as separate colors on the display.

As the specimen is scanned in the Y-direction, the transmitted light detector 34 detects whether a particular pixel is fully transparent. Only at such fully transparent pixels are reflected light intensity measurements taken and digitized. At such pixels, the reflected light intensity is determined and digitized. This is suggested by the depiction at the bottom of FIG. 10, where during the time that the scan is passing across the non-transparent feature 164, as determined by the output of detector 34, the output of detector 36 is ignored. From the intensity value, and from the Y-coordinate of the pixel, together with the values of A, w and $I_o$ determined during the calibration, electronic subsystem 20 determines D in Equation 2 and the corresponding path length variation at the pixel, i.e., the height d of the feature surface above plane 174.

In practice, the specimen substrates are not likely to be perfectly parallel to the image plane, nor is the substrate likely to be perfectly flat. However, these variations are gradual.

It is anticipated that various alterations and modifications thereof will be apparent to those skilled in the art. For example, to avoid the need to sweep the laser beam during the scanning operation, instead of using a linear detector in the preferred embodiment, one could use a time delay integrating sensor or a charge coupled device (CCD) sensor known to those skilled in the art. With such modification, if a laser is used as the light source, coherence in the Y-direction would have to be destroyed by using a rotating ground glass. The coherence in the X-direction is destroyed by the time delay integrating sensor.

The system further includes an inspection system and method that represents a major departure from the traditional die-to-die comparison method of substrate inspection. With the well known and widely used die-to-die (or die-to-data base) comparison technique, the characteristics of the substrate under inspection are compared to another like substrate or a data base that is known to be correct. That requires the simultaneous processing of the same information with two optical columns for the die-to-die for both the die under inspection and the sample to which it is being compared which is both hardware and computer processing intensive.

As will be seen in the discussion that follows, the system may perform all of the inspection tasks using only a single optical column and only the substrate to be inspected. This is accomplished by analyzing the relationship between two or more of the transmitted and reflected light signals from that substrate and derived functions of those signals, the relationship between those light signals, and the relationship between each of the transmitted and reflected light signals and the second derivatives of those light signals.

Flux Inspection

Rather than inspect and compare the results of the foregoing in a pixel-to-pixel comparison, the system determines the presence of contacts and identifies contacts based on the light intensity received. FIG. 11 presents an alternate flow diagram of the present system. With a test image 1101 and reference image 1102 scanned, the reference image 1102 is aligned to the test image to produce an aligned reference image 1103. Thresholds are applied to the aligned reference image 1103 and the test image to determine the presence and identity of contacts. The result of the thresholding is a contact region mask 1105 and 1106, Once these regions are established, the system collects flux in these areas for both the test and aligned reference images at aligned reference flux collection point 1105 and test flux collection point 1106. These elements scan each image in the established contact regions and establish boundaries by comparing the intensity differences and dropoffs with reference to one another as well as reference to applicable thresholds. Tight borders are established using these flux collection elements, and differencer, threshold, and defect detection (DTDD) block 1107 computes the difference in the bordered regions, computes which contacts on the surface exceed a predetermined threshold, and identify defects where thresholds are exceeded.

Figure 13:
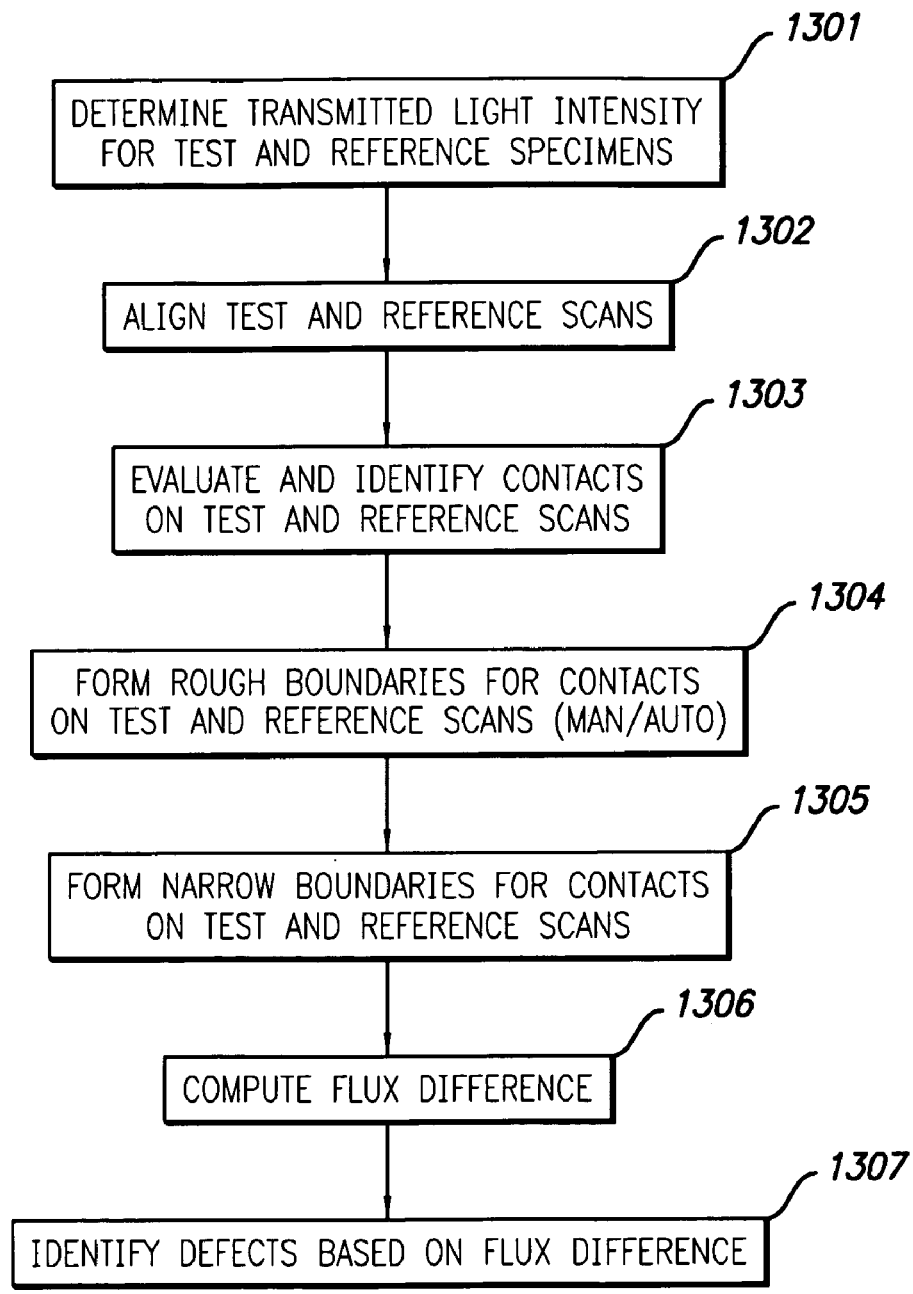
FIG. 13 illustrates an alternate flow diagram of the system.

An alternate representation of system operation is illustrated in FIG. 13. From FIG. 13, the system scans the Test and Reference specimens and determines the transmitted light intensity for both the Test and Reference specimens at point 1301. The system subsequently aligns the scans at point 1302. Alignment may be performed by different algorithms, but the intent of the alignment is to initially orient the two specimens in an identical manner and subsequently to match the scanned images as closely as possible, compensating for rotation, translation, and possibly depth differences between the scanted transmitted images. The system then determines the points on the two scans that are contact points, where contact points are those locations where groups of pixels have higher intensities. Scanning for contacts at point 1303 is typically performed by performing a pixel-by-pixel scan and identifying particular pixels or groups of pixels having a light intensity exceeding a particular threshold.

Once the contacts have been identified, the system associates those pixels forming contacts by correlating pixels exceeding a threshold, or grouping pixels exceeding a certain threshold. Association or grouping of pixels may be performed by an operator, such as by the operator bounding the contacts to be examined, or may be done in an automated manner, such as establishing a fixed box size to be employed around all contacts encountered on a particular specimen, or some other border establishing procedure. Point 1305 illustrates forming boundaries within the borders manually or automatically established at point 1304 enclosing the contact pixels. These boundaries may comprise regularly or irregularly shaped zones tracing approximate outside bounds of the contacts. Point 1305 requires an additional pixel by pixel scan comparison to determine the edges of the contacts, typically signified by dropoffs in light intensities within a predetermined range. For example, if the intensity drops off between two adjacent pixels by a large amount, essentially indicating a transition from contact to a non-contact region, such a dropoff or exceedence of a difference threshold indicates the transition to a non-contact region. Large and small in this context are relative terms; a dropoff of 25 percent over a five or less pixel range, for example, may indicate an edge of a contact. The foregoing is meant by way of example and not limitation, where different types of edge calculation may be employed, such as single pixels or groups of pixels being below a predetermined value, and so forth. The lack of a dropoff or exceedence of a difference threshold may indicate that the pixel remains part o the contact region. In practice, contacts have various types of edges, and the difference between a contact and a non contact region may be the result of a gradual sloping of the material. In such a situation, multiple pixel comparisons may be made, as intensity may not transition from roughly white to roughly black in one, two, or even more pixels. Nonetheless, clustered pixels of high intensity indicate the presence of a contact on both the Test and the Reference specimen. The result of the inquiry at point 1305 is a set of locations identifying where contacts exist on the Test and Reference specimens, and the approximate extent or boundaries of the contacts.

Figure 12:
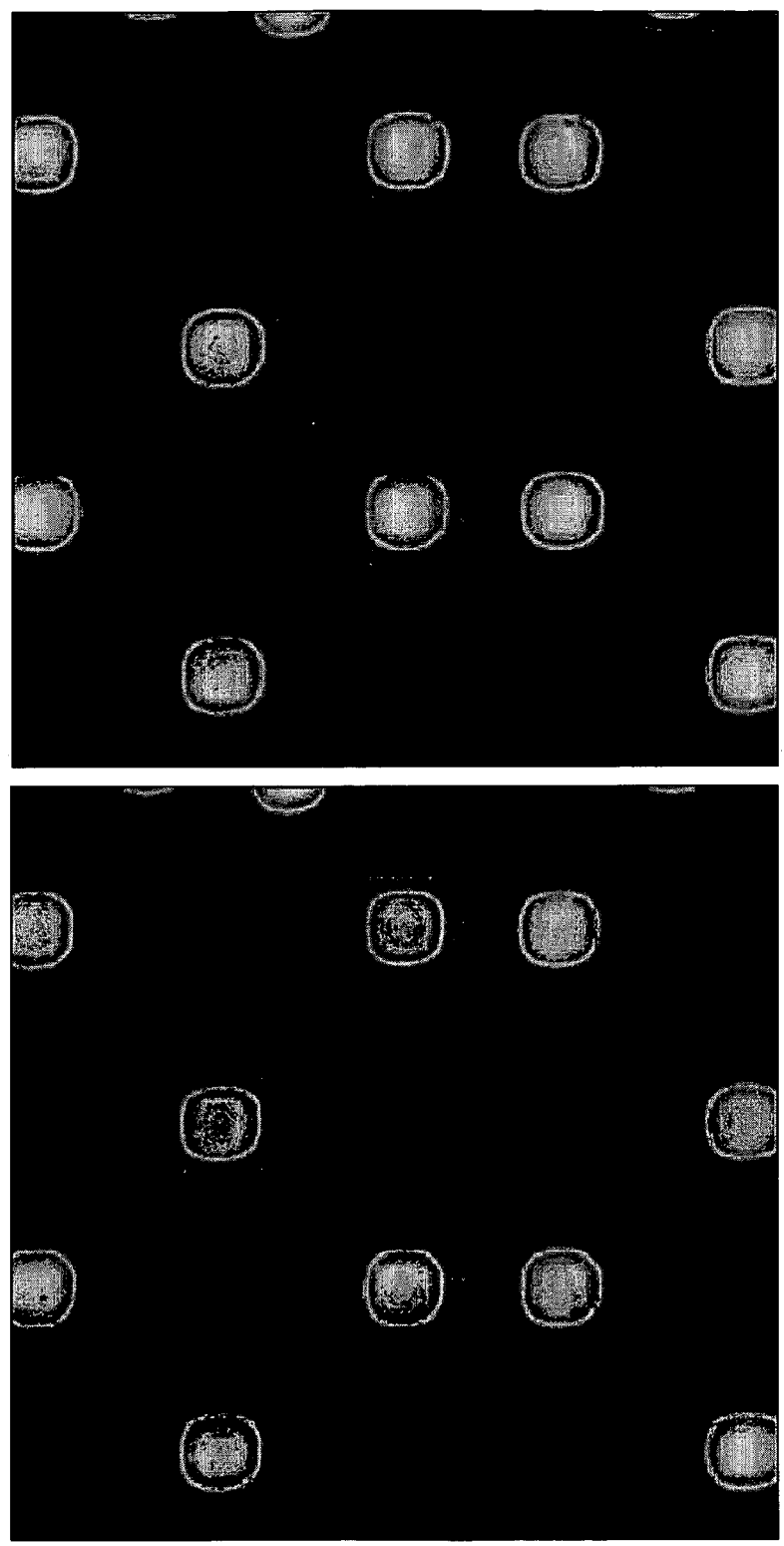
FIG. 12 represents large boxes used for manual measurement during defect review and smaller boxes based on the defect detection design presented, with the smaller boxes around the test and reference scan contact regions.

Boundaries are lines or line segments identifying the outside edge of contacts and are coextensive for both the Test and the Reference specimen. Once the system determines what may be considered an edge, including multiple pixels forming a line where adjacent pixel intensities drop off by a significant amount or to a significant level, the system establishes that line to be a boundary. In the current design, it is anticipated that the boundary overlaps with pixel boundaries. A sub-pixel border may be employed, but such a determination may take additional processing. Boundaries are further established by particular region dropoffs in intensity, and thus may include irregular x-y line segments, such as the boxes around the contacts illustrated in FIG. 12. The intent is to trace the contact outer edge for the Test and Reference specimens as closely as possible, with as little non-contact intensity within the boundaries as possible. The narrow boundaries are overly inclusive rather than under inclusive, meaning if a dispute between the Test and Reference borders would exist (an edge is shifted on the Test from the same position on the Reference, or vice versa), then the larger narrow boundary would be drawn and employed.

Once the narrow boundaries have been established, which are again identical for both the Test and Reference specimen, the system measures the difference in transmission flux between the test and reference images at point 1306. The relative flux difference is given by:

$$\Delta flux = \frac{\left|\sum_{x,y} (I_T - I_R)\right|}{\sum_{x,y} (I_T + I_R)/2}$$

where $I_T$ is intensity at pixel x,y on the test die, and $I_R$ is intensity at pixel x,y on the reference die.

The foregoing summation has a tendency to minimize noise effects, such as residual mis-alignment, and establish non-random defects in the contacts. All bordered regions may be inspected in a single inspection with reasonable post-scan timing. If the difference between the Test and Reference scans exceed a certain threshold, then the contact may be considered defective and this contact defect may be subsequently addressed.

Point 1307 represents a determination of defects on the Test and Reference scan related to the contacts. This defect determination may be performed in various ways, as described below, including but not limited to computing a flux for each region. Defect determination may be performed in a variety of ways, including but not limited to computing the flux difference between the Test and Reference region according to the equation presented above and comparing this difference to the minimum, maximum, or mean fluxes of the two regions. Minimum, maximum, and mean fluxes may be computed in a pixel-by pixel manner, evaluating all pixels for maximum or minimum values, or computing the mean by summing all pixels and dividing by the number of pixels examined. Other techniques may be employed while still within the scope of the present invention.

Establishment of narrow boundaries in the manner presented enables inspection of oddly or arbitrarily shaped contacts using the flux determination method outlined above. Inspection of irregularly shaped contacts has been difficult in the past, and usage of flux differences in the present design enables inspection of contacts having shapes that differ from the norm, such as the previously used golden contact.

Bounded regions are established as follows. The entire image is binary-thresholded to zero and one, Equal to or above the threshold is 1, below the threshold is 0. The contact pixels have already been identified at this point. The system rasters the reference and test images from left to right, and from top to bottom (e.g. 1,1; 1,2; 1,3; . . . 1,n; 2,1; 2,2; etc.). If the greyscale of a pixel is substantially equal to 1, and its top and left pixel are both 0, then the scan is entering a contact region and a new region tag is assigned. If one of the two adjacent pixels (top and left) has a tag, that tag is assigned to the pixel. If the top and left pixels have tags that are different, the top tag is assigned to the pixel, and the two tags are marked equivalent, signifying that the tagged regions are actually one region. The equivalence table is then made unique, or those areas having more than one tag tags and determined to form one contact are combined into a single contact area, and the area assigned a unique tag. The system then retags all pixels with the appropriate contact identification information.

The present system may use the flux determination scheme alone with a transmitted representation of the Test and Reference scans, or with a reflected representation of the Test and Reference scans. Use of a reflected representation may requires an alternate set of thresholds and requirements, but would operate in substantially the same manner as the transmitted Test and Reference flux determination described above. The design may use both transmitted and reflected images of the Test and Reference specimens to more accurately determine the narrow boundaries presented and more accurately determine the flux for specific contacts. Further, the flux determination may be employed by itself in an inspection device or may be used in connection with a design that uses both transmitted and reflected light to scan the specimen for, for example, pattern defects. Such a system may create a two dimensional transmitted and reflected representation of the surface to determine particular feature aspects, and the flux determination aspect may be employed to augment this feature aspect determination. For example, a system may use transmitted and reflected light to determine pattern or other feature defects, and this may be combined with the present flux determination aspect to find contact defects. The transmitted and reflected light scanning may be performed simultaneously, or it may be performed with staggered timing, such as with the reflected scan occurring before or after the transmitted scan.

Figure 14:
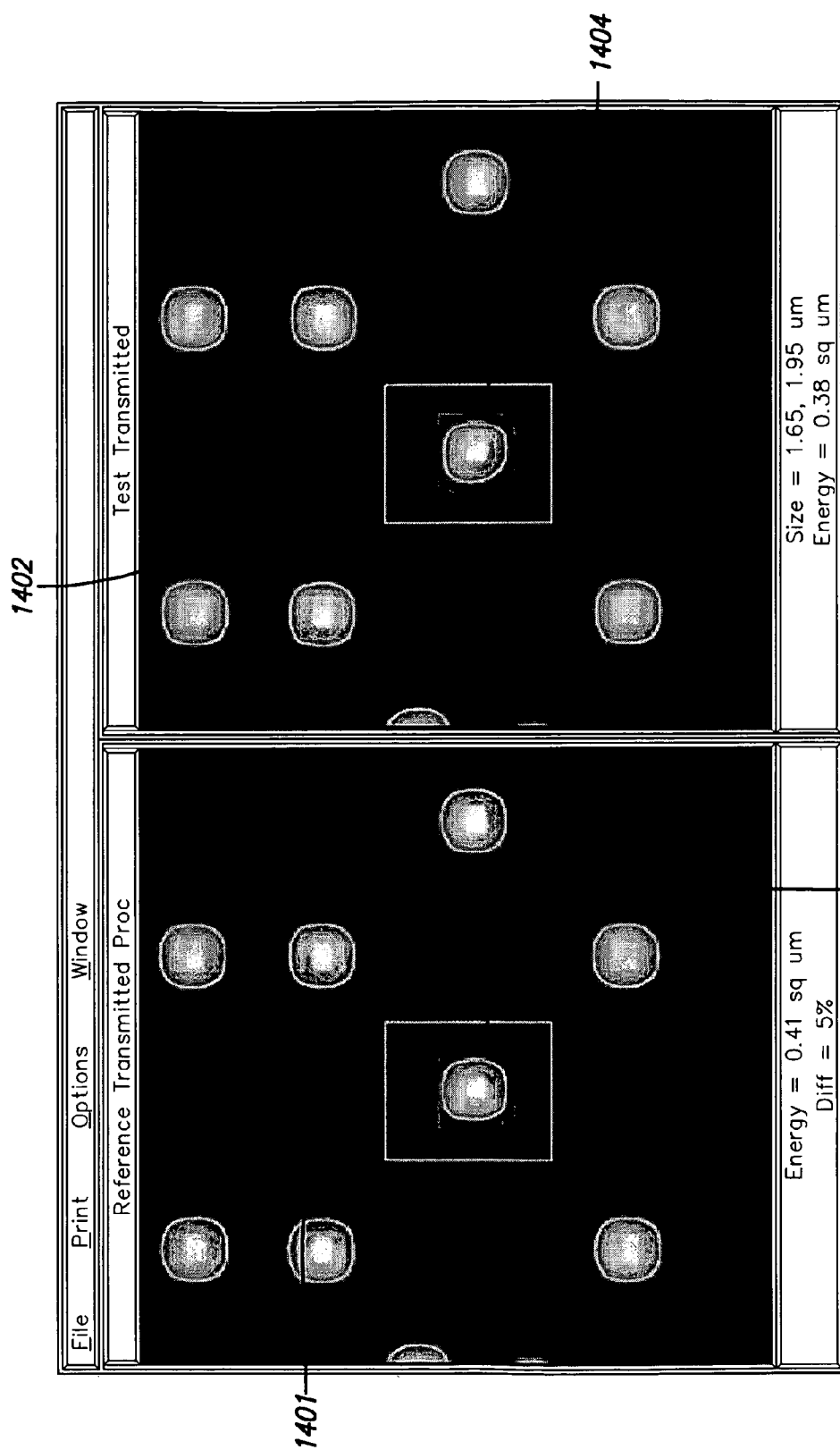
FIG. 14 illustrates two transmitted scans, one reference photomask transmitted scan and one test photomask transmitted scan.
Figure 15:
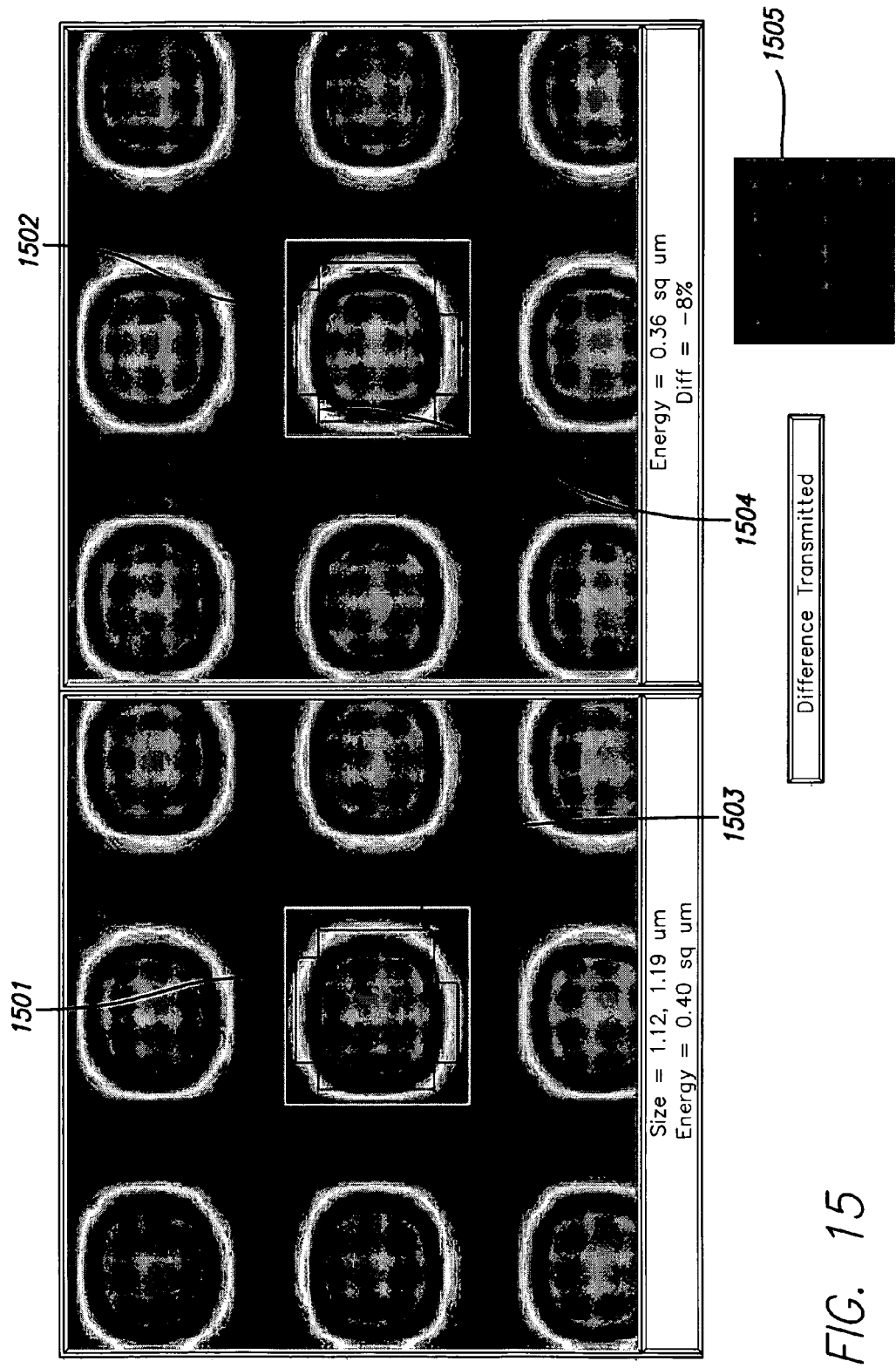
FIG. 15 is a further illustration of identified contacts with broad outside borders and narrowed interior borders.

FIG. 14 illustrates two transmitted scans, one a reference photomask transmitted scan and the other a test photomask transmitted scan. The large rectangular borders 1401 and 1402 indicate the manually or automatically selected regions for flux calculation during defect review. The tighter borders 1403 and 1404 indicate those borders determined by the system to constitute approximate edges of the contact, and generally are formed by intensity transitions from brightness to darkness. FIG. 15 is a further illustration of identified contacts with broad outside borders 1501 and 1502 and narrowed interior borders 1503 and 1504. Representation 1505 is the difference when the two bounded regions 1503 and 1504 are subtracted. This difference is compared against either a threshold or a predetermined pattern representing a known type of defect to determine whether any errors are present. Alternately, the total sum difference within the bounded region may be computed, and a percentage difference between the two contacts determined. The total flux difference for the tightly bounded area is divided by the average flux for the entire bounded area, and the system may determine that a defect exists if the total flux divided by the average flux is above a certain threshold, a defect exists. Different thresholds or defect detection schemes may be employed, including but not limited to considering a defect to exist when approximately a five percent difference exists between measured flux and average flux in a tightly bounded region.

Figure 16:
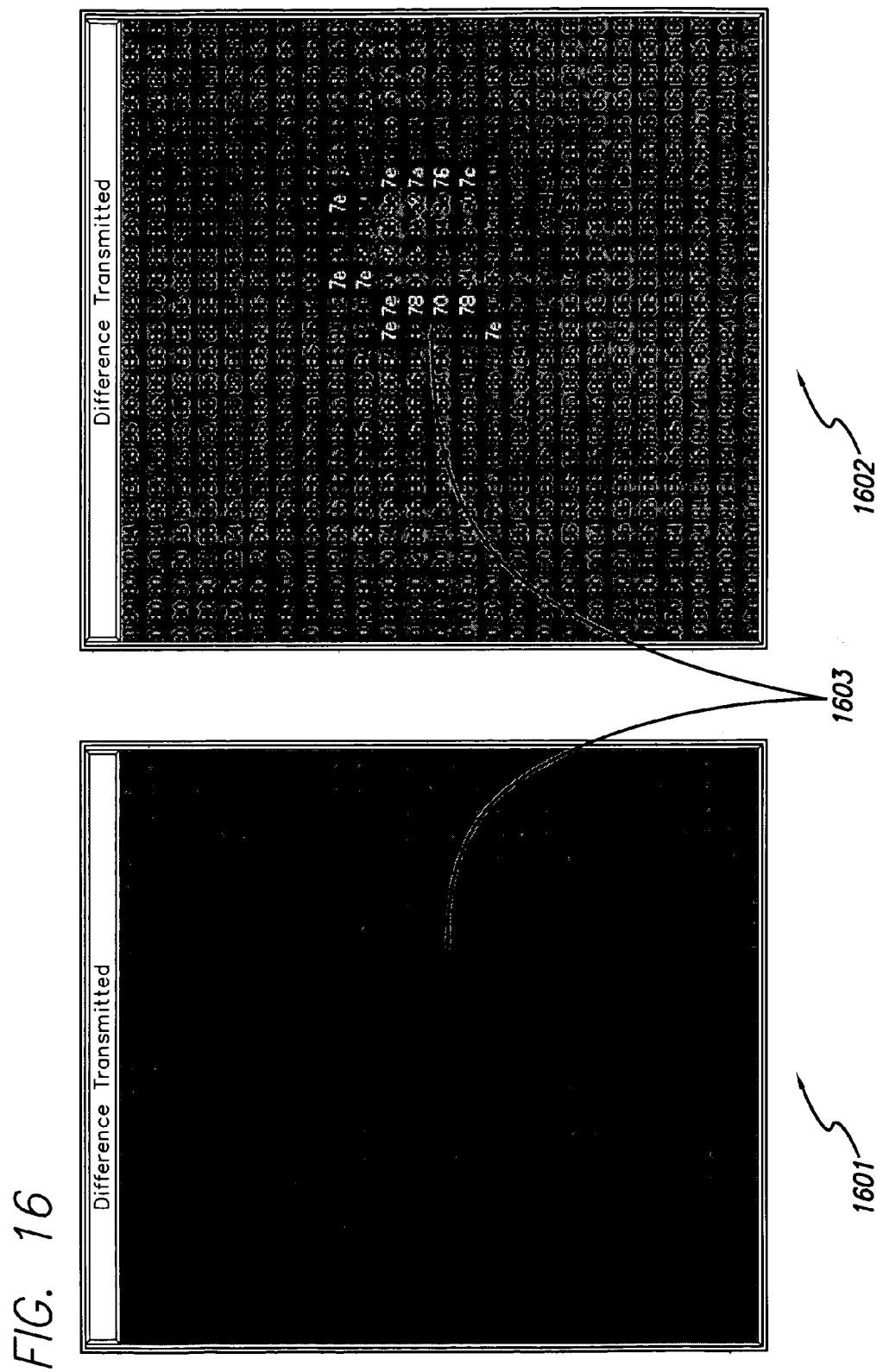
FIG. 16 represents graphical flux differences between pixels and numerical differences between pixels for test and reference specimens within the established narrow boundary.

FIG. 16 presents a graphical representation and a numerical representation of a transmitted energy difference based on computed flux between a Reference photomask and a Test photomask. The graphical representation 1601 illustrates that color differences, or light intensity differences, exist for certain pixels in the scans, while the numerical representation 1602 includes values representing hexadecimal intensity values, where "80" corresponds to a zero difference between Test and Reference scanned intensity values. Inside the narrow boundary, difference intensities range from 7a–a2, and certain 7e difference pixels exist outside the narrow boundary 1603. The presence of differences 7a–a2, when taken over the average difference within the region, may be considered a defect. If the average in the region is 80, or zero, the difference |7a–80|/(a2–7a), or 80/(80–7a) or 80/(a2–80) or some other value, such as absolute difference, versus total difference or other values may indicate the presence of a defect. Pixel measurements over a certain threshold may indicate the presence of a defect, such as a five percent difference between largest measured pixel and average measured pixel values.

Further, with the present flux determination aspect of the design, defect sizes are reported using a flux difference ratio, and highlighting of defects covers the contacts entirely. This improves over the general case previously employed, which highlights defects on a pixel-by-pixel basis.

Again, although the invention has been described using transmitted light, it is readily extended to use reflected light, or a combination of the two, and may operate on reverse-tone photomasks where contacts are opaque or have lower transmission.

While the invention has been described in connection with specific aspects thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

What is claimed is:

1. A method for inspecting a plurality of specimens, each specimen having at least one feature located thereon, comprising:
    scanning each specimen using both transmitted and reflected light energy, thereby establishing a plurality of points, each point having an intensity associated therewith;
    determining bounded regions wherein said intensities differ relatively significantly from other regions on the specimen;
    calculating a flux based on intensities within said bounded regions, said flux calculated based on properties in bounded regions of all specimens; and
    determining defective features on the specimens based on the flux difference between bounded regions of the specimens.

2. The system of claim 1, wherein said defective feature determining comprises computing a flux difference between said plurality of specimens and an average flux level, and identifying those features having a ratio of flux difference to average flux level exceeding a predetermined threshold.

3. A method for determining contact defects in a plurality of semiconductor wafer dice, comprising:
    scanning the semiconductor wafer dice using transmitted and reflected light energy, resulting in scanned representations of said semiconductor dice;
    aligning the scanned semiconductor dice;
    selecting approximate potential problem areas on said plurality of scanned semiconductor dice;
    establishing a set of boundaries within each of said scanned semiconductor dice, wherein said establishing comprises locating demarcations of intensity variations; and
    comparing fluxes between regions within said sets of boundaries to determine contact defects.

4. The method of claim 3, wherein said selecting is performed manually.

5. The method of claim 3, wherein said selecting is performed automatically.

6. The method of claim 3, wherein said contacts are irregularly shaped.

7. A system for determining defects in a plurality of specimens, comprising:
    at least one sensor for sensing transmitted and reflected light received from each specimen, said sensor transmitting a light intensity representation of one specimen to a computing device, wherein said computing device comprises:
        an aligner for aligning the light intensity representations of a plurality of specimens;
        a critical point selector for selecting general areas for detailed inspection on said light intensity representations of a plurality of specimens;
        a boundary device for creating a set of narrow boundaries around each of said critical points based on light intensity transitions; and
        a flux computer for computing the flux associated with the critical points within the narrow boundaries of the light intensity representations.

8. The system of claim 7, wherein said critical points comprise openings on the specimen.

9. The system of claim 7, wherein said critical points comprise contacts and said plurality of specimens comprise a plurality of semiconductor masks.

10. The system of claim 9, wherein defect sizes related to said contacts are reported as a ratio of flux difference, and entire contacts are highlighted for review.

11. A method for determining contact defects for arbitrarily shaped contacts in a plurality of semiconductor wafer specimens, comprising:
    scanning the semiconductor wafer specimens using transmitted and reflected light energy scanning, resulting in scanned representations of said semiconductor wafer specimens;
    aligning the scanned semiconductor wafer specimens;
    selecting bounded areas on said plurality of scanned semiconductor wafer specimens;
    establishing a set of boundaries within each of said scanned semiconductor wafer specimen bounded areas, wherein said establishing comprises locating demarcations of intensity variations; and
    comparing fluxes between regions within said sets of boundaries to determine contact defects for arbitrarily shaped contacts.

12. A method for inspecting a specimen, comprising:
    scanning the specimen using transmitted and reflected light energy;
    forming boundaries representing specific areas on the specimen;
    analyzing the scans using the boundaries to determine defects, wherein said analyzing comprises determining the flux associated with the specimen.

13. The method of claim 12, wherein said transmitted light inspection is simultaneous with said reflected light inspection.

14. The method of claim 12, wherein said transmitted light inspection occurs at a different time from said reflected light inspection.

* * * * *